United States Patent [19]

Engell et al.

[11] Patent Number: 4,686,012
[45] Date of Patent: Aug. 11, 1987

[54] ION-SELECTIVE MEASURING ELECTRODE DEVICE

[75] Inventors: John E. Engell, Rungsted Kyst; Svend Mortensen, Copenhagen, both of Denmark

[73] Assignee: Radiometer A/S, Copenhagen, Denmark

[21] Appl. No.: 914,550

[22] Filed: Oct. 1, 1986

Related U.S. Application Data

[63] Continuation of Ser. No. 750,974, Jun. 28, 1985, abandoned, which is a continuation of Ser. No. 626,707, Jun. 29, 1984, abandoned, which is a continuation-in-part of Ser. No. 000,101, Oct. 31, 1983, abandoned.

[30] Foreign Application Priority Data

Oct. 29, 1982 [DK] Denmark .............................. 4800/82
Jul. 4, 1983 [DK] Denmark .............................. 3087/83

[51] Int. Cl.⁴ ...................... B01D 54/40; G01N 27/46
[52] U.S. Cl. ...................................... 204/1 T; 204/419
[58] Field of Search ...................... 204/1 A, 1 T, 419; 501/134, 153, 154

[56] References Cited

U.S. PATENT DOCUMENTS 3,143,488  8/1964  Arthur .................................. 204/1 A
4,021,325  5/1977  Pungor ................................. 204/419
4,083,764  4/1978  Van de Leest ....................... 204/419
4,111,777  9/1978  Dobson ............................... 204/419

FOREIGN PATENT DOCUMENTS 0067274  12/1982  European Pat. Off. ............ 423/306
3013677  10/1981  Fed. Rep. of Germany .
2052462   1/1981  United Kingdom .

Primary Examiner—John F. Niebling
Attorney, Agent, or Firm—Stiefel, Gross, Kurland & Pavane

[57] ABSTRACT

An ion-sensitive measuring electrode device with an ion-sensitive element based on ion-conducting crystalline ceramic material is provided. The electrode device shows a selectivity to the Na$^+$ ion versus the H$^+$ ion corresponding to the selectivity of the known sodium-sensitive glass-based solid membrane electrodes.

Ion-sensitive measuring electrode devices showing good selectivity properties are provided on the basis of ion-conducting crystalline material, the crystal structure of which comprises a three-dimensionally extending interstitial space containing positions for the ion, especially material in which the interstitial space has bottlenecks which just permits passage of the ion.

A method for preparing polycrystalline ceramic material based on oxides of zirconium, phosphor and silicon is also provided.

11 Claims, 13 Drawing Figures

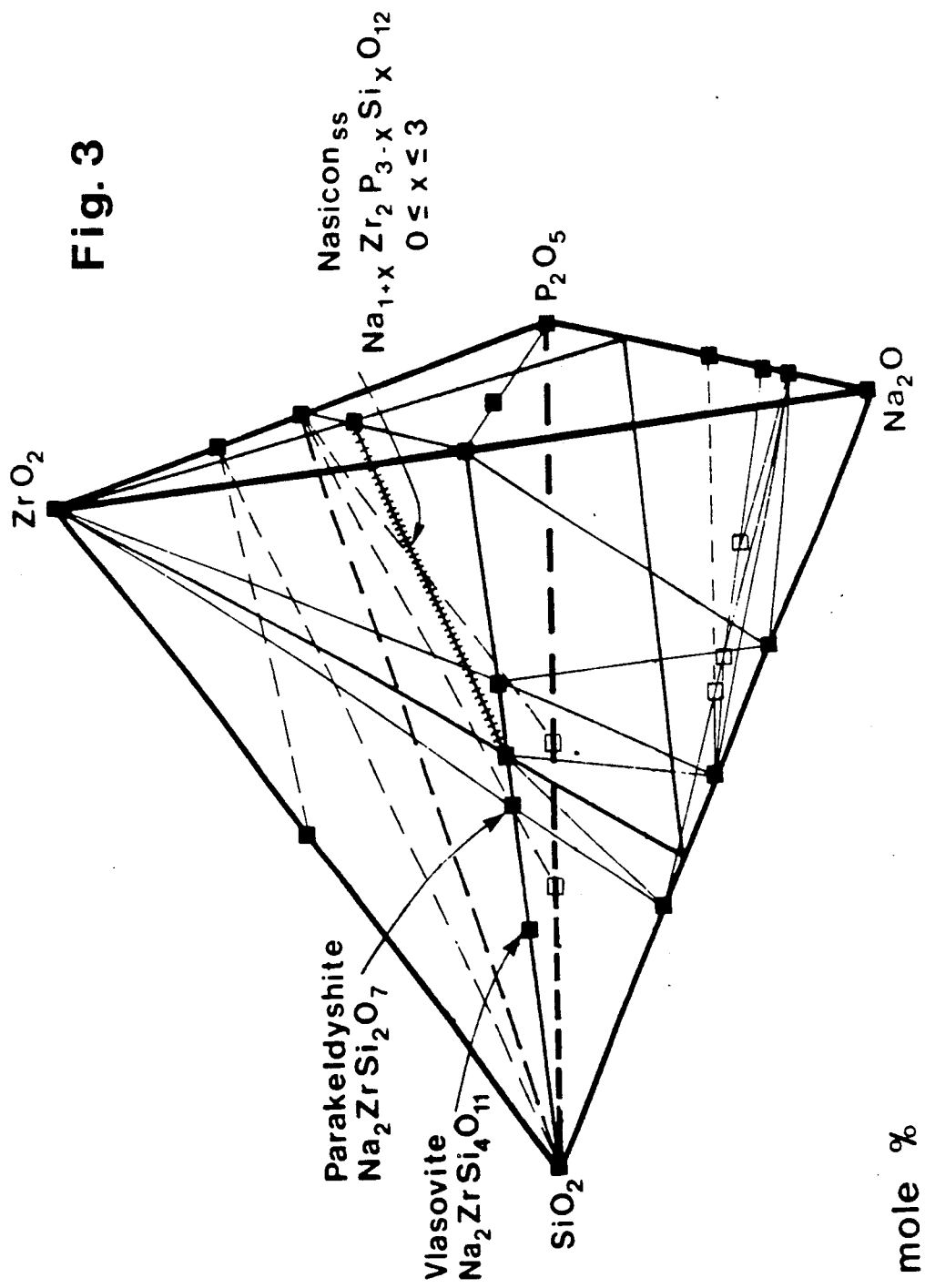

ION-SELECTIVE MEASURING ELECTRODE DEVICE

This is a continuation of U.S. application Ser. No. 750,974, filed June 28, 1985, now abandoned, which was a continuation of U.S. application Ser. No. 626,707, filed June 29, 1984, now abandoned, which was a continuation-in-part of PCT/OK 83/00101, filed Oct. 31, 1983, now abandoned.

The present invention relates to an ion-sensitive measuring electrode device comprising an ion-sensitive solid element showing selectivity for a particular ion species and reference system.

The ion-sensitive measuring electrode device according to the invention is characterized in that the ion-sensitive element is constituted by or comprises an ion-conducting crystalline material, the crystal structure of which comprises a three-dimensional interstitial space comprising positions for the ion.

Such ion-sensitive elements are novel. Up to now, solid membrane electrodes have primarily been based on single crystals, the ion conductivity of which is based on impurities in the crystal lattice, or on glasses.

Among the materials showing a crystal structure of the above-mentioned type are materials which are suitable for being shaped as polycrystalline bodies (tablets) by ceramic working, and such tablets are suitable for use in connection with the preparation of measuring electrodes.

Especially, it has been found that in the case where the three-dimensional interstitial space has bottleneck passages, which just permit passage of the ion, it is possible to prepare ion-sensitive electrochemical measuring electrode devices with ion-selective properties; thus, sodium-sensitive measuring electrodes with good selectivity properties to $Na^+$ ions versus $H^+$ ions have been manufactured.

Representatives of the above-mentioned materials with three-dimensional interstitial space are found among ceramic materials based on oxides of zirconium and phosphorus and/or silicon.

Polycrystalline ceramic materials and materials with three-dimensional interstitial space are known from e.g. German published specification No. 2,634,289 (ref. 1), from Materials Research Bulletin 11, 1976, p. 173, (ref. 2), European published patent specification No. 46.932 (ref. 3), and Solid State Ionics 3/4, (1981), pp. 215-218 (ref. 4). A number of materials, including the Nasicon mixture series $Na_{1+x}Zr_2Si_xP_{3-x}O_{12}$, in which $0 \leq x \leq 3$, methods for preparing the materials and their use in electrochemical batteries are known from these references. However, the fact that among the materials described there are also materials, which in addition to ion-conductivity also show selectivity to the ion species in question, is a surprising recognition, which opens new possibilities for making ion-selective measuring electrodes in which the ion-selective element has a low impedance and is therefore less demanding with respect to the attached measuring equipment and shielding against noise than the presently used corresponding glass-based ion-selective measuring electrode devices. In addition, the electrode response will be fast because of the high ion conductivity.

A measuring electrode device with an ion-sensitive element in the form of a polycrystalline ceramic material of the composition $Na_{2.94}Zr_{1.49}\text{-}Si_{2.2}P_{0.8}O_{10.85}$—also designated $ZrO_2$-deficient Nasicon or NZPS-82-1BC has been found useful for determining the $Na^+$ ion with satisfactory selectivity characteristics versus $H^+$ ions. It is also contemplated that ion-sensitive measuring electrode devices with selectivity towards also other ions than the sodium ion and based on polycrystalline ceramic materials with crystal structure of the type described in the above-mentioned literature references can be made.

Interesting possibilities are to produce ion-selective measuring electrodes with selectivity to other alkali metal ions by replacing the $Na^+$ ion in the crystal structure with other alkali metal ions. Another interesting possibility would be to make a hydrogen ion-sensitive measuring electrode by using Keldyshite, which is the $H^+$ form of Parakeldyshite, cf. FIG. 3, of the ion-sensitive element.

It should be noted that the electrochemical measuring electrode devices according to the invention may be in the form of both traditional measuring electrodes with liquid or gelled electrolyte between the ion-sensitive element and the reference electrode and electrodes with solid state contact to the ion-sensitive element. Furthermore, both single rod electrodes and combination electrodes combined with an exterior reference electrode system may contain the ion-sensitive element.

The ion-sensitive element in the form of a compressed and sintered polycrystalline tablet of ceramic material may easily be mounted at the end of a tubular stock tube, e.g. of plastic material, using epoxy or the like.

The ceramic material of the ion-sensitive electrode device according to the invention may, e.g., be prepared by preparing a gel by controlled mixing, in an organic medium, of anhydrous phosphoric acid with lower alkoxides of zirconium, silicon and an alkali metal and optionally a lower alkoxide of aluminium, the alkali metal component alternatively being an alkali salt soluble in the organic medium, followed by gelling by addition of water, removing water and volatile components from the gel, and converting the water- and volatiles-free gel to a ceramic material.

The method makes it possible to prepare a very finely grained polycrystalline material, cf. FIG. 2, with a structure which secures good material properties, e.g. workability to thin plates with thicknesses down to 0.6 mm. Under suitable pressure and sintering conditions, the material may be prepared in a very dense form with closed porosity of less than about 5%. Furthermore, the method of the invention has made it possible to provide Nasicon- or $ZrO_2$-deficient Nasicon, which is sintered completely at temperatures between 1000° C. and 1100° C., i.e. temperatures considerably below the temperature where incongruent melting takes place. Therefore, the sintered product will not show inclusions of crystalline $ZrO_2$.

Interesting polycrystalline materials for use as ion-sensitive elements in the electrode device of the invention are stated in claims 5-9.

The drawings of Nasicon crystal structures given in Materials Research Bulletin 11, 1976, pp. 173-182 shows the three-dimensional interstitial space containing the $Na^+$ ion. There will be seen various positions between which the $Na^+$ ion may migrate through the material, since each $Na(1)$ position is connected three-dimensionally with two $Na(2)$ positions and four $Na(3)$ positions, and that each $Na(2)$ position and $Na(3)$ position is connected with two $Na(1)$ positions.

For $x=2$ are seen the so-called bottlenecks in Nasicon crystals. These are situated in the interstitial space and are passed by the Na+ ion during position changes. In the bottlenecks there is, in the shown crystal structure, a distance between the centres of two O-ions of 4.95 Å which is very close to the sum of the diameter of the Na+ ion and the diameter of the O$^{--}$ ion, which sum is 4.8 Å.

As will be seen from the experimental data, the polycrystalline material tested not only exhibits ion conductivity for sodium ions, but also a certain selectivity towards these as opposed to protons and other alkali metal ions. It is regarded as probable that it is the presence of the three-dimensional interstitial space with the Na+ ions and bottlenecks contained therein which ensures not only the well-known fast sodium transport, but also the so far unknown selectivity which makes it possible to produce electrochemical measuring electrodes with selectivity characteristics comparable to what has previously been found for known ion-selective glass electrodes for the determination of sodium.

In the following, the invention is further illustrated with reference to the drawing, in which FIG. 1 shows a prototype of an ion-selective measuring electrode device according to the invention;

FIG. 3 shows a phase diagram for the 4-component system $ZrO_2$, $SiO_2$, $Na_2O$, $P_2O_5$;

DETAILED DESCRIPTION OF THE DRAWINGS

Figure 1:
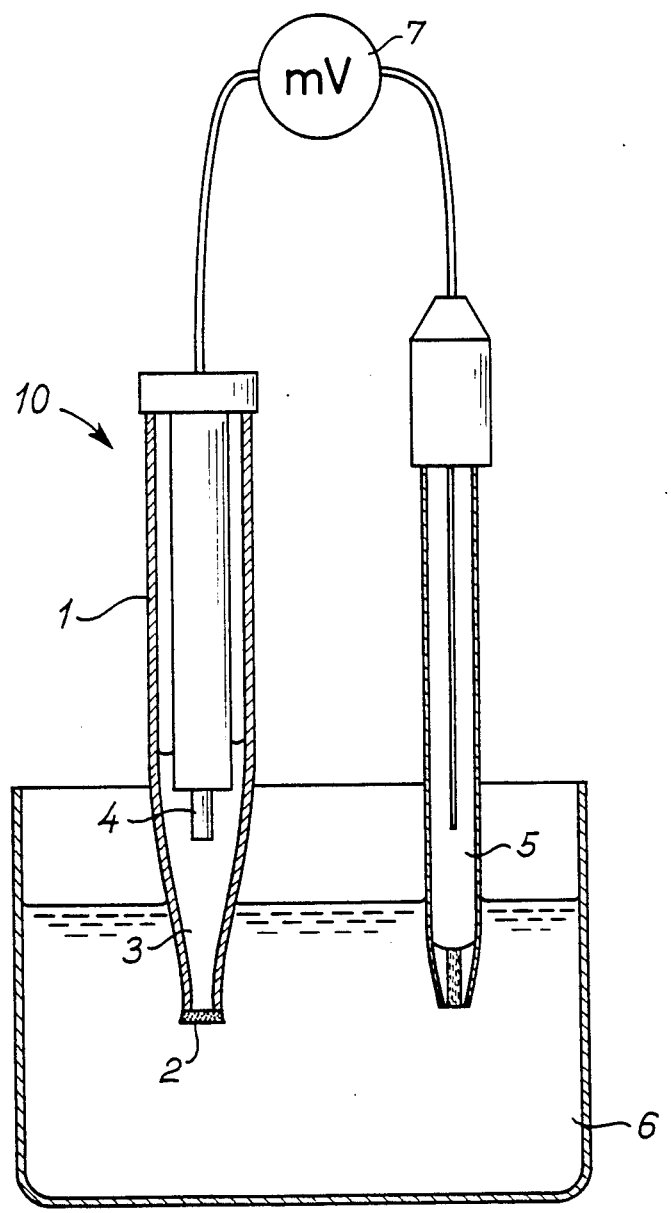

FIG. 1 shows an experimental measuring arrangement comprising an ion-sensitive measuring electrode device according to the invention, generally designated 10. The measuring electrode device according to the invention has a polycrystalline ceramic ion-sensitive membrane 2 in the form of a disc melted into a glass tube 1. The measuring electrode device has an internal reference system consisting of an internal electrolyte 3 and an internal reference electrode 4. Together with a separate reference electrode 5, the measuring electrode device is immersed into a sample solution 6, and on the basis of the potential difference measured by means of the mV-meter 7 over the internal reference electrode and the reference electrode, the content of a particular ion species in the sample solution can be determined. A measuring arrangement of this type wherein the ceramic membrane shows Na+-selectivity is described in greater detail in connection with Example 5 below.

Figure 2A:
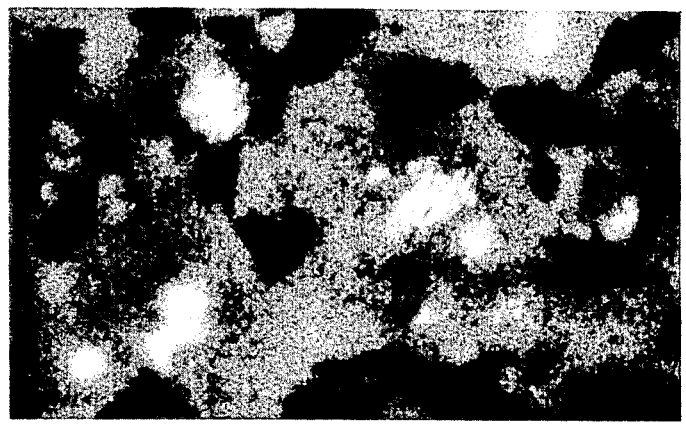
FIGS. 2a and 2b show an electron microscope picture of a surface in a sintered plate of a zirconium-deficient Nasicon material prepared according to the prior art (2a) and prepared according to a preferred embodiment of the invention (2b)

FIG. 2a shows an electron microscope picture of a sectioned surface in a plate of synthetic zirconium-deficient Nasicon ceramic prepared according to the prior art (Materials Research Bulletin 11, 1976, p. 173) by sintering to 1226° C. for 6 hours. The picture width corresponds to 20 μm. The photograph shows white areas and black areas on a grey background. The white areas are free crystalline $ZrO_2$ (Baddeleyite) and the black areas are zirconium-deficient glass, while the light grey mass is crystalline Nasicon with grain sizes in the range of 2–10 μm and a stoichiometric composition corresponding to x=1.89 as determined by X-ray diffraction.

Figure 2B:
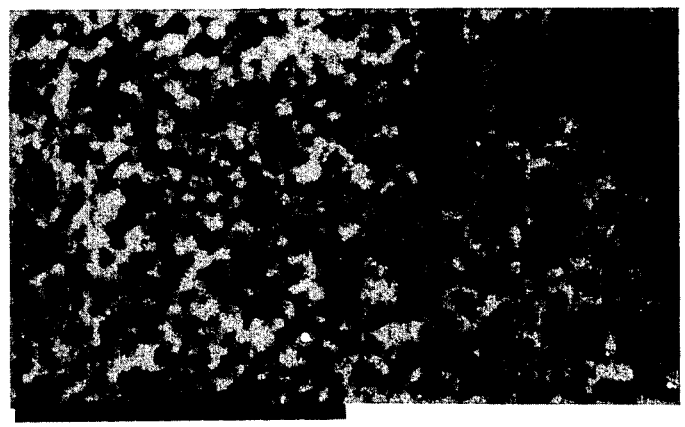

FIG. 2b shows an electron microscope picture of a sectioned surface in a plate of the synthetic $ZrO_2$-deficient Nasicon ceramic designated NZPS-82-1BC prepared according to the gel process of the invention by sintering to 1100° C. for 10 hours. The picture width is again 20 μm. The material is seen to be a polycrystalline ceramic with a grain size less than 1 μm in which no inclusions of crystalline $ZrO_2$ are to be seen. An additional glass phase are seen between the Nasicon crystals. The Nasicon crystals have a stoichiometric composition corresponding to x=2.10 as determined by X-ray diffraction.

FIG. 3 shows a phase diagram for the 4-component system $ZrO_2$, $SiO_2$, $Na_2O$, $P_2O_5$. The composition (on a molar basis) of known crystalline compounds within the system is marked with squares. A complete mixing series between $NaZr_2P_3O_{12}$ and $Na_4Zr_2Si_3O_{12}$ (Nasicon SS) is marked with a hatched line and may be designated $Na_{1+x}Zr_2P_{3-x}Si_xO_{12}$, where $0 \leq x \leq 3$.

Figure 4:
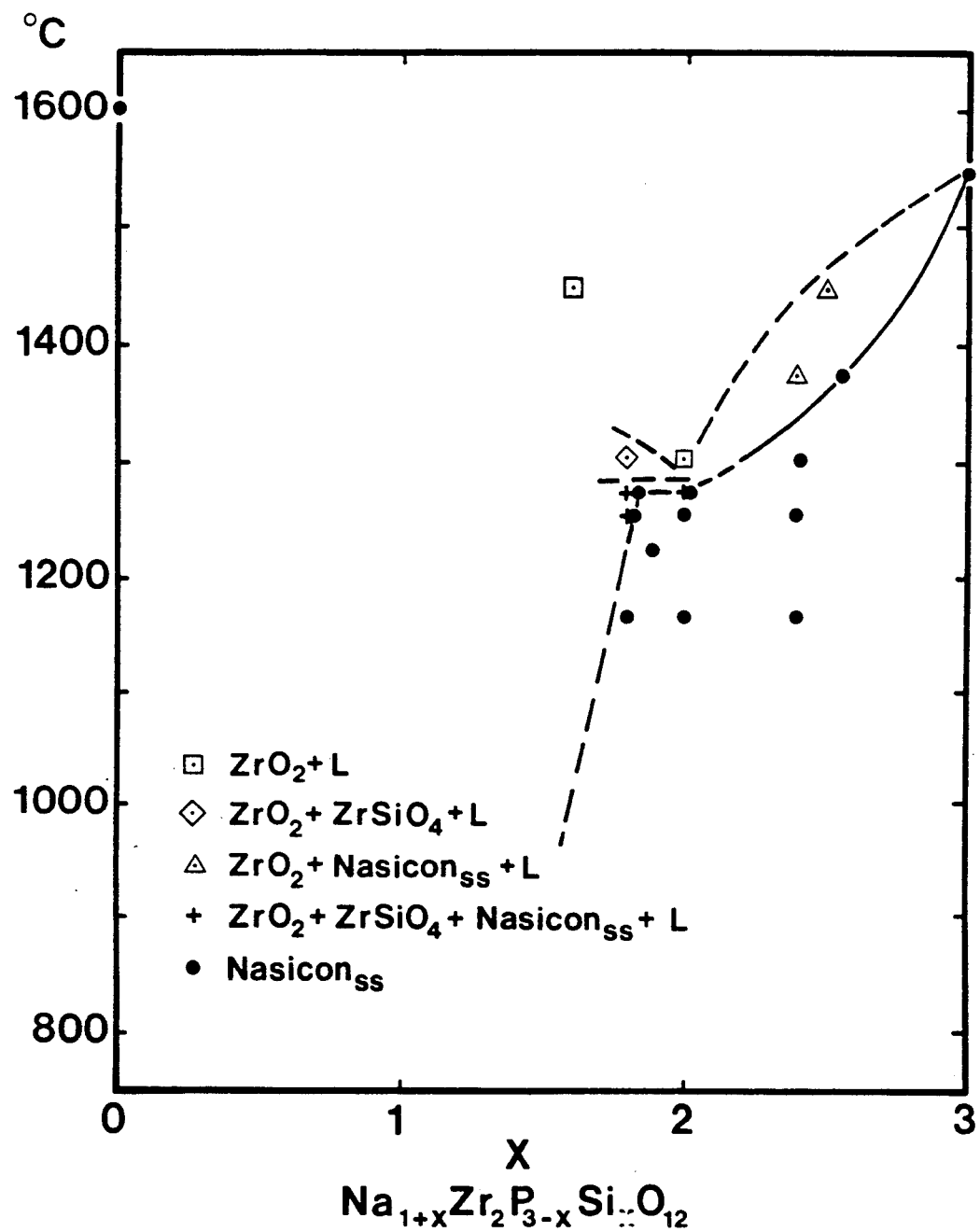
FIG. 4 shows an excerpt of the phase diagram corresponding to the Nasicon mixing series.

FIG. 4 shows an excerpt of the phase diagram corresponding to the Nasicon mixing series. The diagram shows that Nasicon with a composition corresponding to x=2, in the vicinity of which the Nasicon compounds interesting for battery applications and with a high ion conductivity are situated, melts incongruently at a temperature close to 1276° C. under the formation of a melt $(L) + ZrO_2 + ZrSiO_4 + $ a more silicon-rich Nasicon. At 1300° C. this combination consists of a melt $(L) + $ crystalline $ZrO_2 + $ Nasicon with a composition corresponding to x=2.18. At 1306° C. the combination consists exclusively of a melt $(L) + $ crystalline $ZrO_2$.

Figure 5:
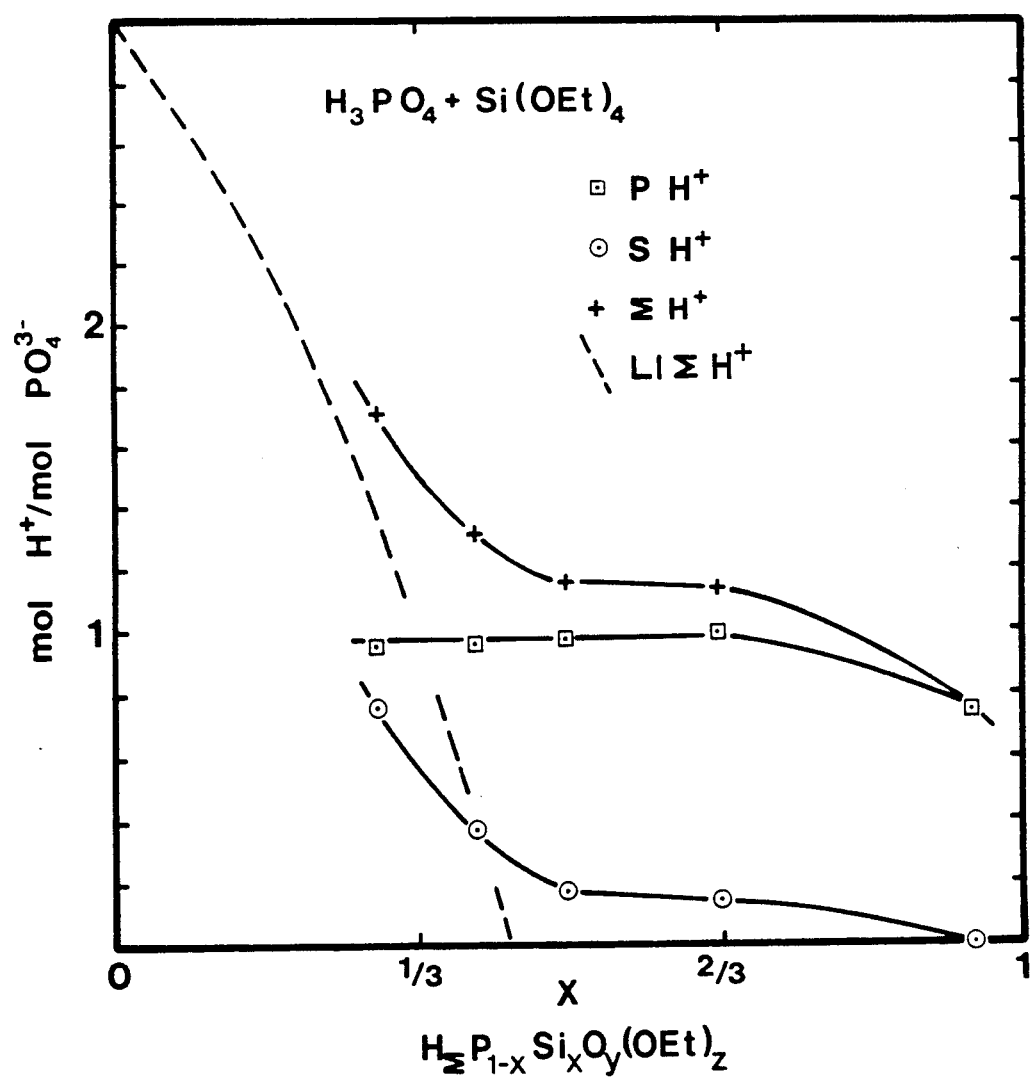
FIG. 5 shows the variation in the number of unreacted HO-groups in mixtures of phosphoric acid and tetraethylorthosilicate.

FIG. 5 shows the variation in the number of unreacted HO-groups in mixtures of $H_3PO_4$ and $Si(OEt)_4$ as a function of composition. The determination of the number of HO-groups was performed by pH-titration using a glass electrode (Radiometer G202B), a calomel reference electrode with a salt bridge of LiCl dissolved in isopropanol (Radiometer K701) and sodium methoxide dissolved in methanol as base. The reaction of the mixture took place at room temperature. In the figure is shown the number of primary hydrogen ions (PH+), the number of secondary hydrogen ions (SH+) and the sum of hydrogen ions (ΣH+). In the Figure, the dotted line designates the lower limit of ΣH+ after complete reaction between phosphoric acid and tetraethylorthosilicate (LlΣH+).

Figure 6:
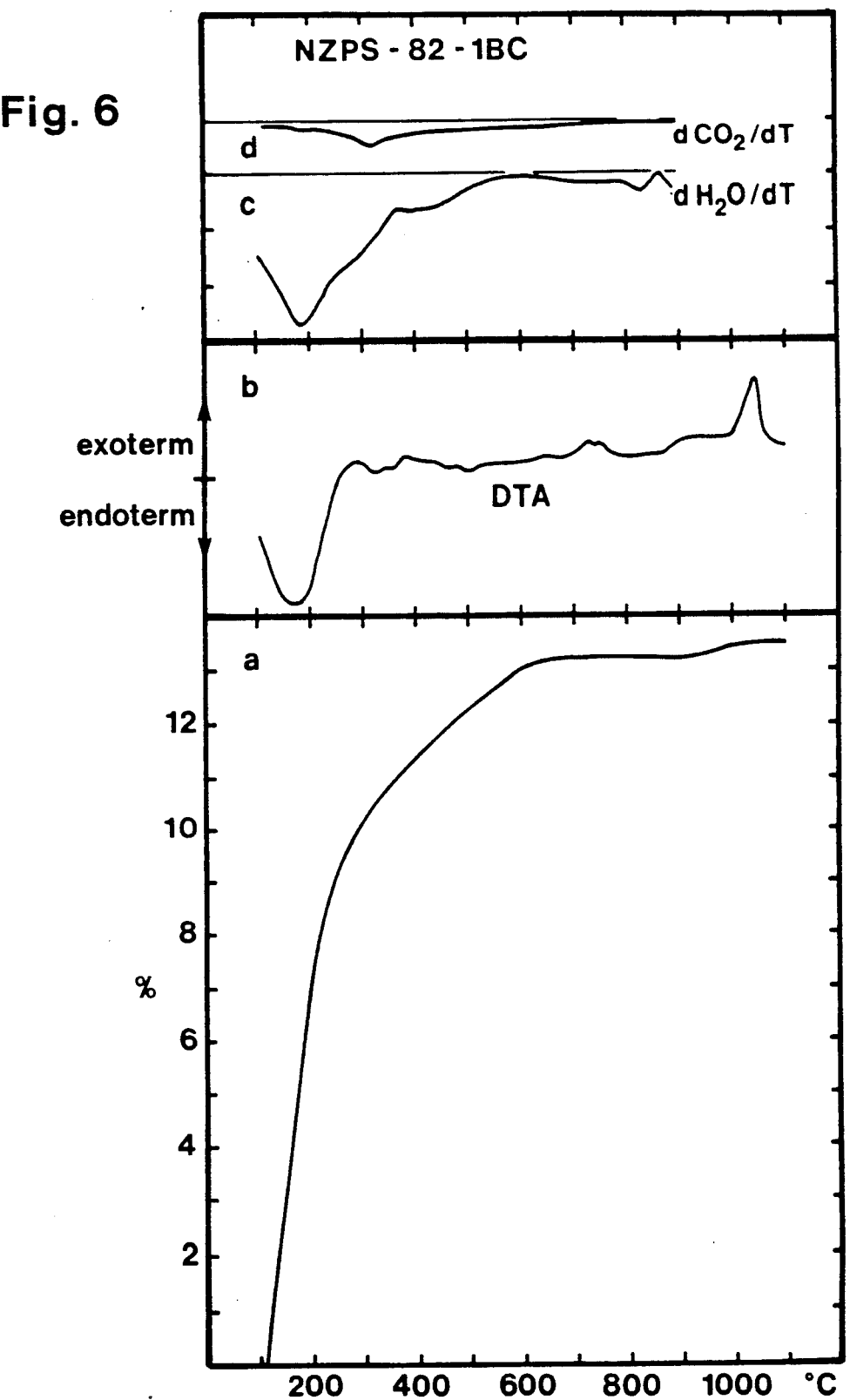
FIG. 6 shows the results of thermogravimetric analysis and differential thermal analysis on the NZPS-82-1BC gel.

FIG. 6 shows results of thermogravimetric analysis and differential thermo analysis on the gel NZPS-82-1BC which had been dried at 110° C. FIG. 7A shows the total weight loss in percent as a function of the temperature. The rate of increase of the temperature was 8° C./minute. FIG. 6B shows a differential thermal analysis curve obtained with a rate of increase of the temperature of 8° C./minute. The curve shows an endotherm maximum around 180° C. corresponding to a maximum in the release of $H_2O$ (this is observed in all the gels). The well-defined exotherm peak at 1040° C. reflexes crystallization of the major part of the glass. FIG. 6C shows qualitatively the differential release of water as a function of temperature at a rate of increase of the temperature of 10° C./minute. FIG. 6D shows qualitatively the differential carbon dioxide release as a function of temperature at a rate of increase of the temperature of 10° C./minute.

Figure 7:
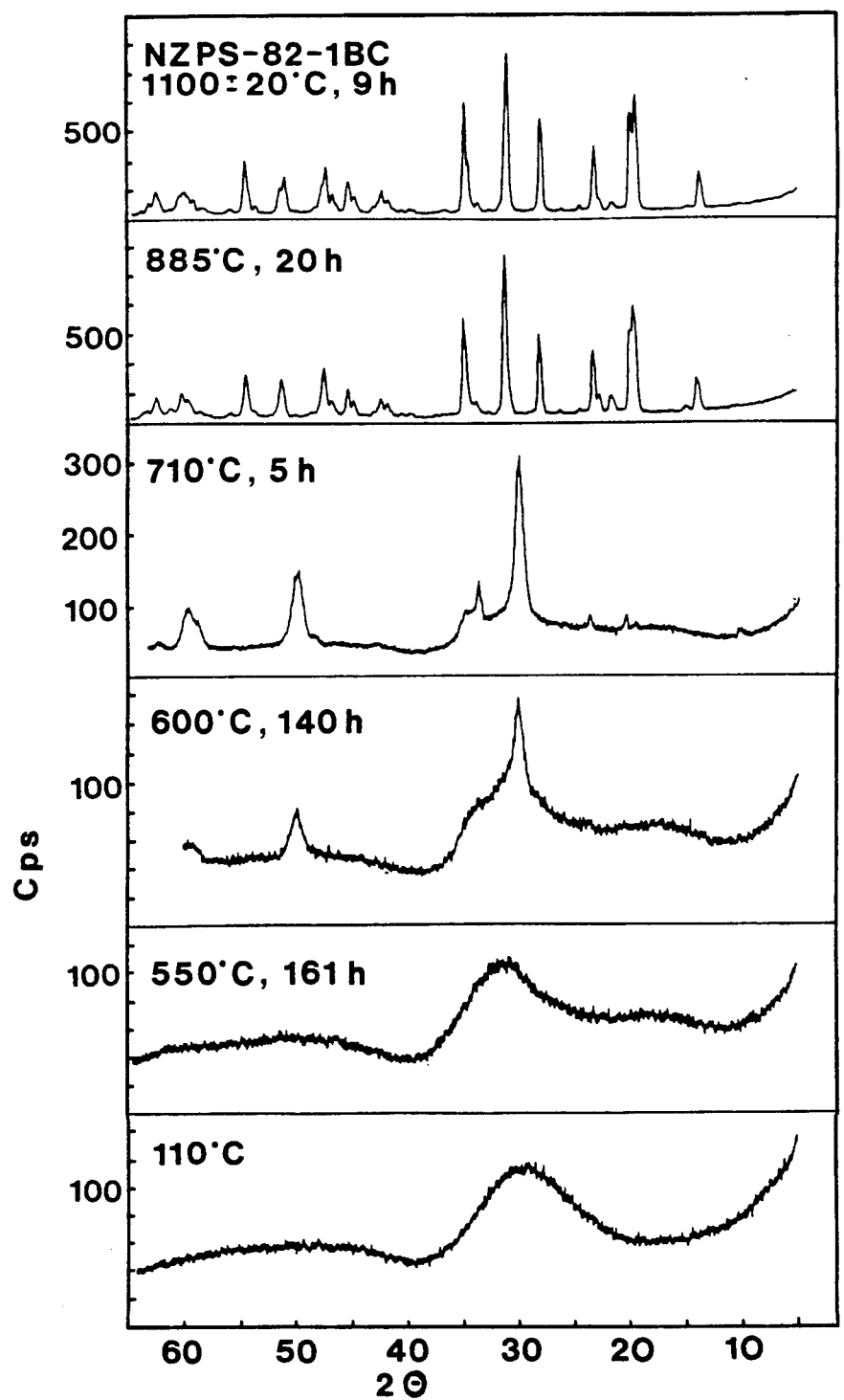
FIG. 7 shows X-ray diffraction diagrams of the NZPS-82-1BC gel heated to various temperatures.

FIG. 7 shows X-ray diffraction diagram of NZPS-82-1BC (vacuum-dried at 110° C.) heated to the indicated temperatures for the indicated time spans. The temperatures were reached according to the following program: 20° C.-710° C. 1° C./minute, 710° C.-930° C. 0.4° C./minute, and above 930° C. 1° C./minute. The broad weak peaks in the XRD-diagram for gel dried at 110° C. are typical for the gels. Heating to 550° C. for 161 hours does not result in any marked changes in the XRD-diagram. Heating to 600° C. for 140 hours results in beginning crystallization as shown by the two narrow peaks. The crystalline phase formed is a tetragonal zirconium-dioxide. Heating to 710° C. for 5 hours also results in a partial crystallization of the gel. The phase formed is tetragonalzirconium dioxide. Heating to 885° C. or above results in the formation of crystalline Nasicon.

Figure 8:
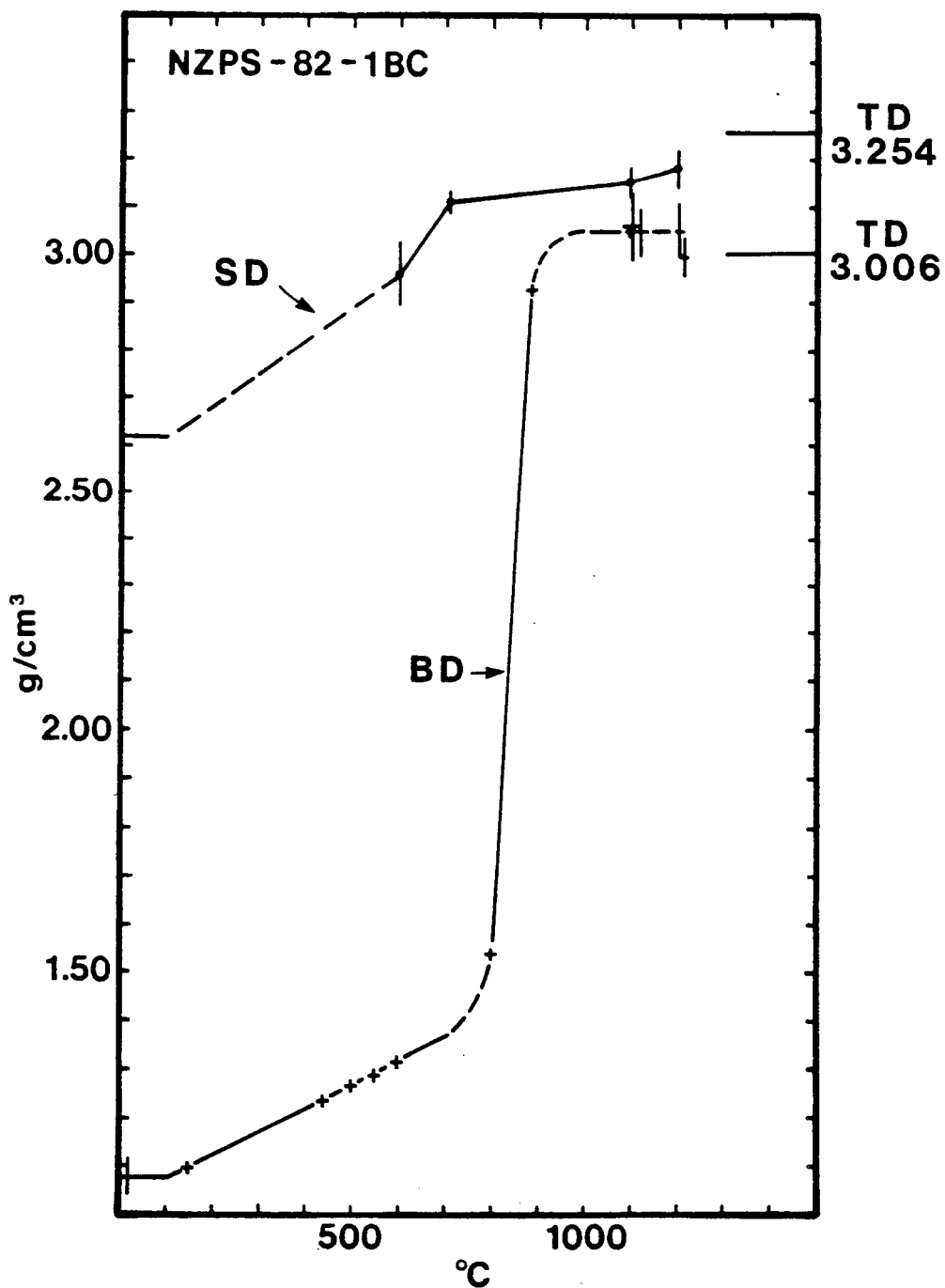
FIG. 8 shows the sintering behaviour of plates pressed from crushed gel of NZPS-82-1BC.

FIG. 8 shows the sintering course for plates pressed from the material NZPS-82-1BC produced by the process of the invention and pressed at 95 MPa from gel dried at 110° C. The changes in specific density (SD) and bulk density (BD) are shown. The plates were heated according to the following program: 20°-710° C. 1° C./minute, 710°-930° C. 0.4° C./minute, and above 930° C. 1° C./minute. It may be seen from the bulk density curve that the substantial sintering occurs at temperatures in the range of 800°-900° C. and that the bulk density at 1110° C. constitutes some 97% of the theoretical density (TD). In the figure are furthermore given the theoretical densities of Nasicon ($Na_{3.1}Zr_2P_{0.9}Si_{2.1}O_{12}$) and Vlasovite ($Na_2ZrSi_4O_{11}$), (the theoretical densities being 3.254 and 3.006, respectively), which are the equilibrium phases for the composition in question at 1100° C.

Figure 9:
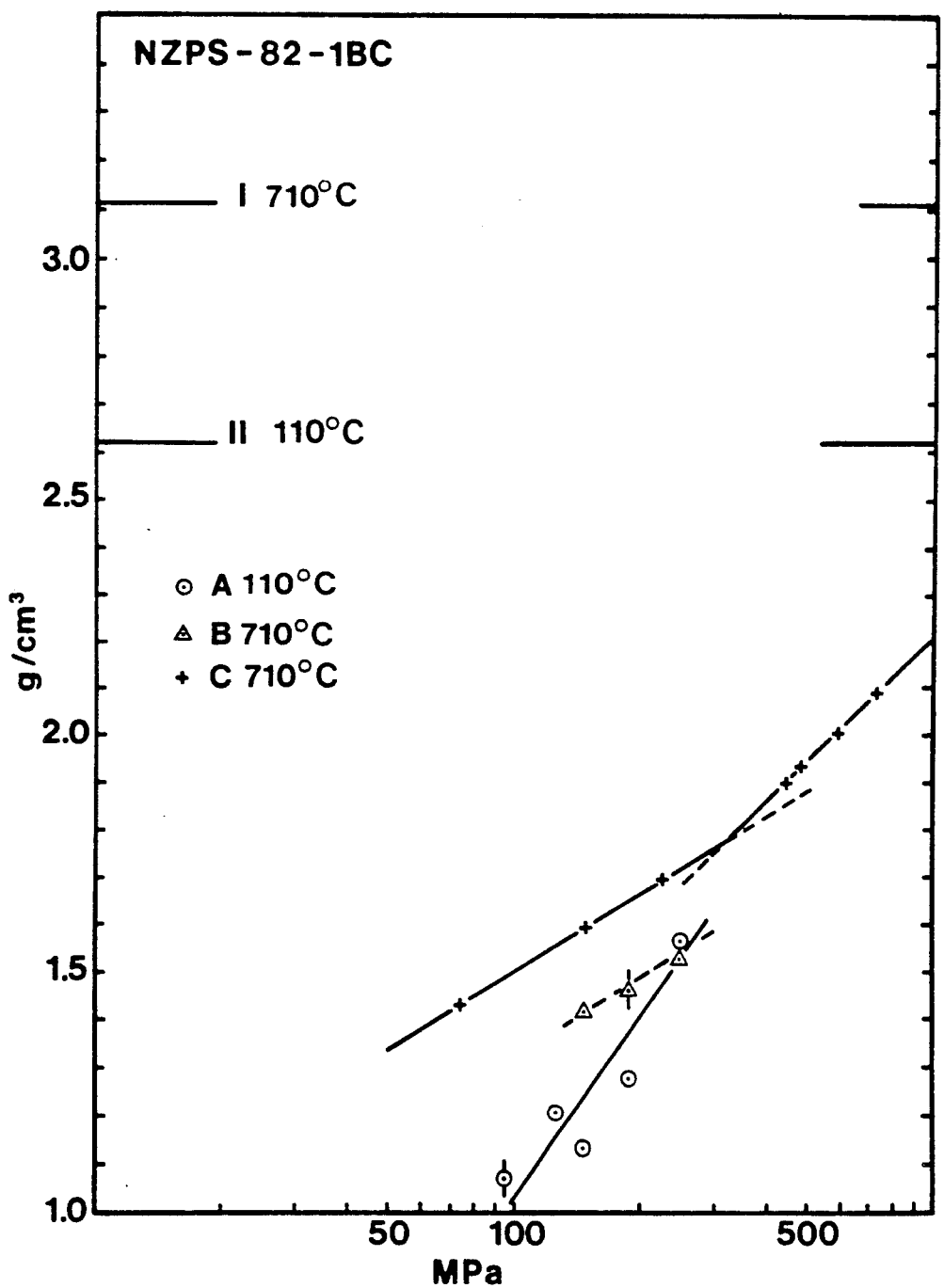
FIG. 9 shows the density of the gel NZPS-82-1BC subjected to different treatments and the bulk density of plates prepared from the thus treated gel material.

FIG. 9 shows (for the material NZPS-82-1BC) the specific density of gel dried at 110° C. (2.61 g/cm$^3$, marked I 710° C.) and of gel calcinated at 710° C. (3.1 g/cm$^3$, marked II 110° C.) as well as the green bulk density as a function of pressing pressure for crushed gel dried at 110° C. (marked A 110° C.) or calcinated at 710° C. (marked B 710° C.), respectively, or calcinated at 710° C. and thereafter crushed (marked C 710° C.).

Figure 10:
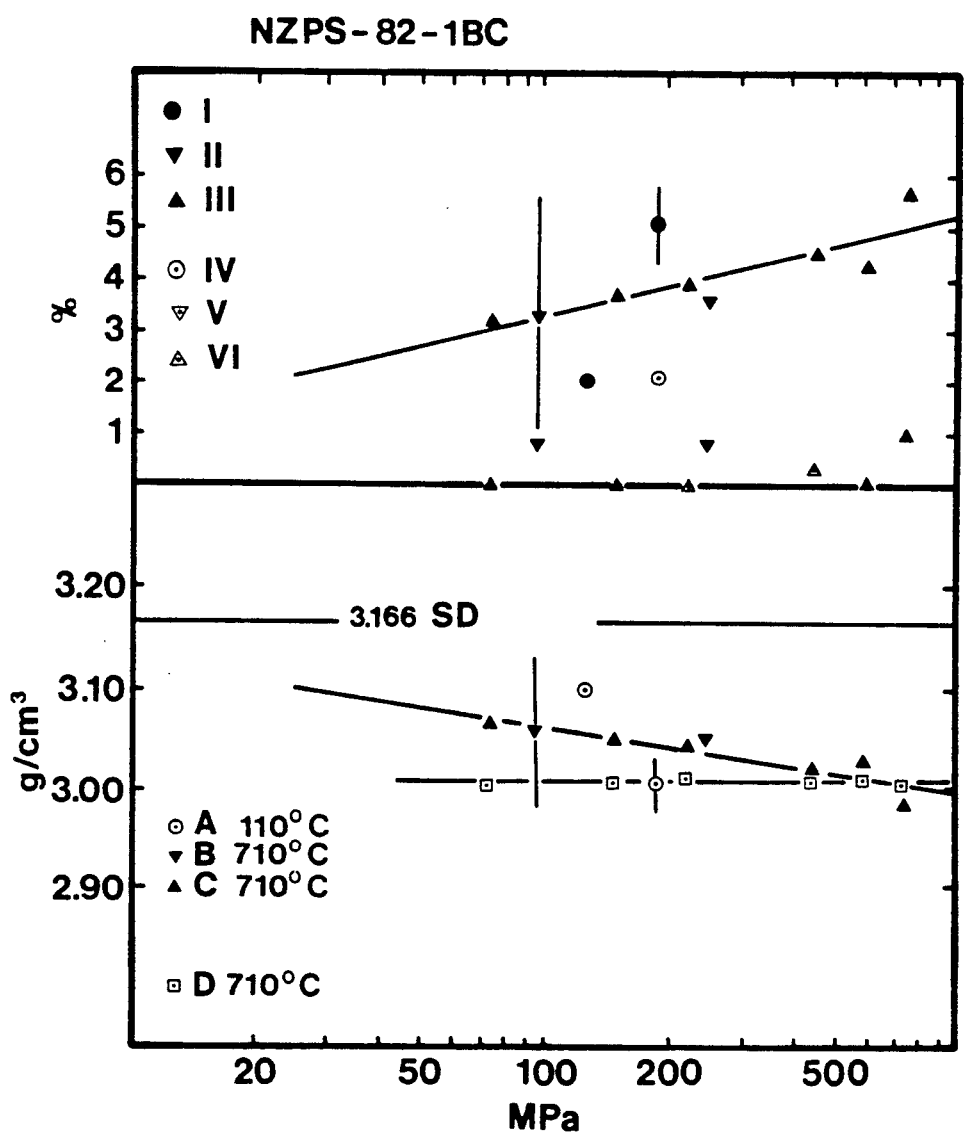
FIG. 10 shows the bulk density of the corresponding sintered plates as a function of the pressing pressure and the sintering conditions.

FIG. 10 shows the bulk density and the porosity of the corresponding sintered plates as a function of the pressure when pressing the plates (before the sintering). The sintering was performed at 1100±20° C. The top half of FIG. 10 shows the open and the total porosity for the samples I-III and IV-VI, respectively, as a function of the pressing pressure. Samples I and IV were prepared from crushed gel dried at 110° C., samples II and V from crushed gel calcined at 710° C., and samples III and VI from gel calcined at 710° C. and then crushed. The open porosity corresponds to surface irregularities on the plate and is quite low, while the total porosity is 3-5% and increases with increasing pressing pressure. The bottom half of FIG. 10 shows the bulk density of the sintered plates. Sample A was prepared from crushed gel dried at 110° C., sample B from crushed gel calcined at 710° C., and sample C from gel calcined at 710° C. and then crushed. Samples A, B, and C were sintered in air. Sample D was prepared from gel calcined at 710° C. and then crushed, and the sintering was performed in vacuum.

Figure 11:
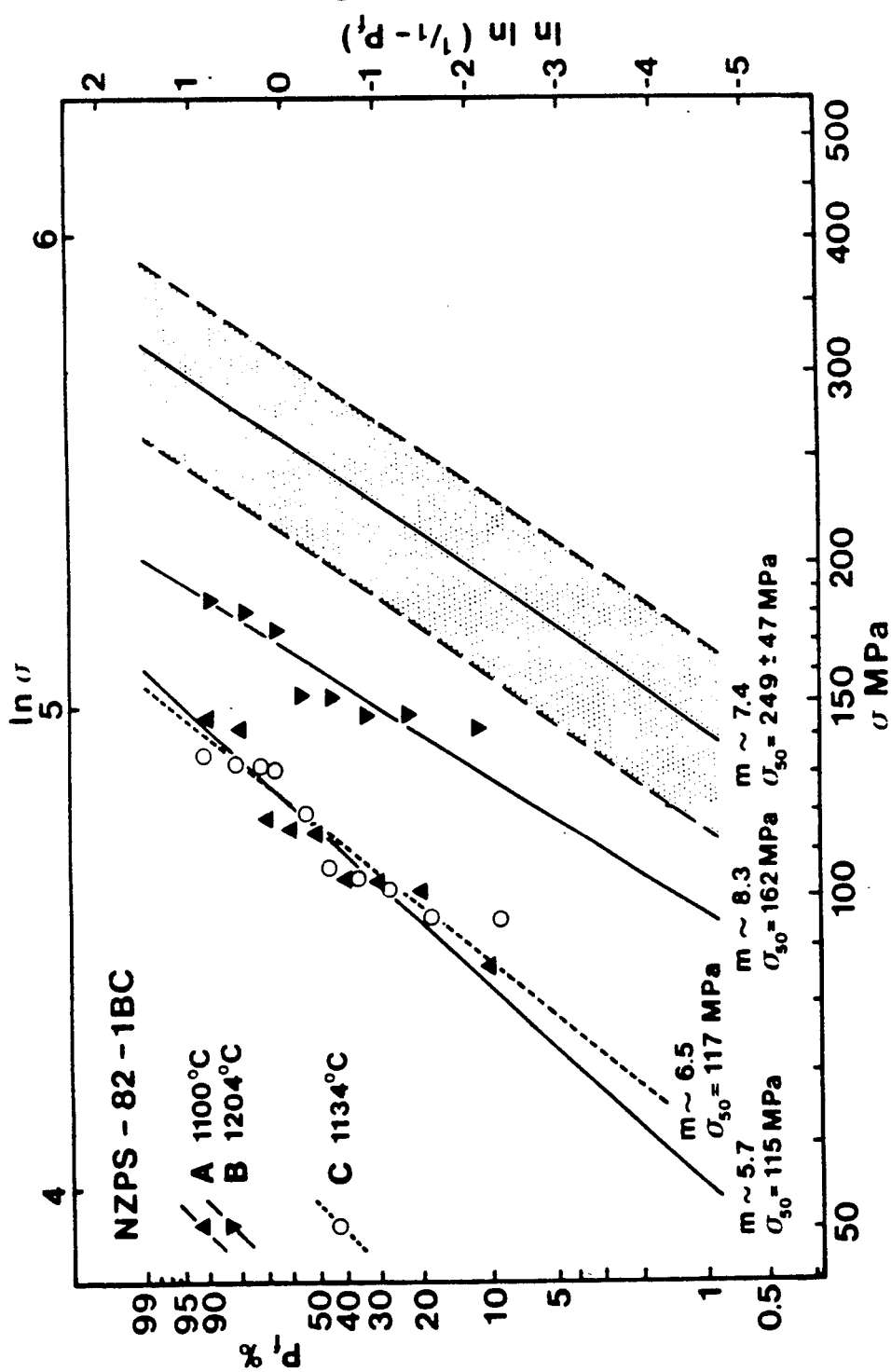
FIG. 11 is a Weibul-plot, which for a sample shows the fracture probability $P_f(\%)$ as a function of the loading in a three-point bend/tensile strength test.

FIG. 11 shows a Weibul-plot of the fracture probability $P_f(\%)$ as a function of the loading ($\sigma$) of the sample (sintered plates from NZPS-82-1BC) by a three-point bending method. The sample marked A 1100° C. was sintered at 1100° C., while the sample marked B 1204° C. was sintered at 1204° C. Both samples were sintered in air and both samples had a specific volume of 0.07 cm$^3$. The data points for the two samples were subjected to regression analysis resulting in the two full-drawn lines passing through the data points. The sample marked C 1134° C. was sintered in vacuum at 1134° C. and had a specific volume of 0.09 cm. Regression analysis of the data points resulted in the dotted regression line. For comparison purposes, the shaded area outlines strength test data for $\beta''$-alumina specimens with a specific volume of 0.05 cm$^3$ (cfr. Trans. Brit. Ceram. Soc. 79, 1980, pp. 120-127). The relatively low fracture strengths of the samples are due to the presence of closed pores up to 0.1 mm in size. These pores can probably be removed by optimizing the processing conditions.

Figure 12:
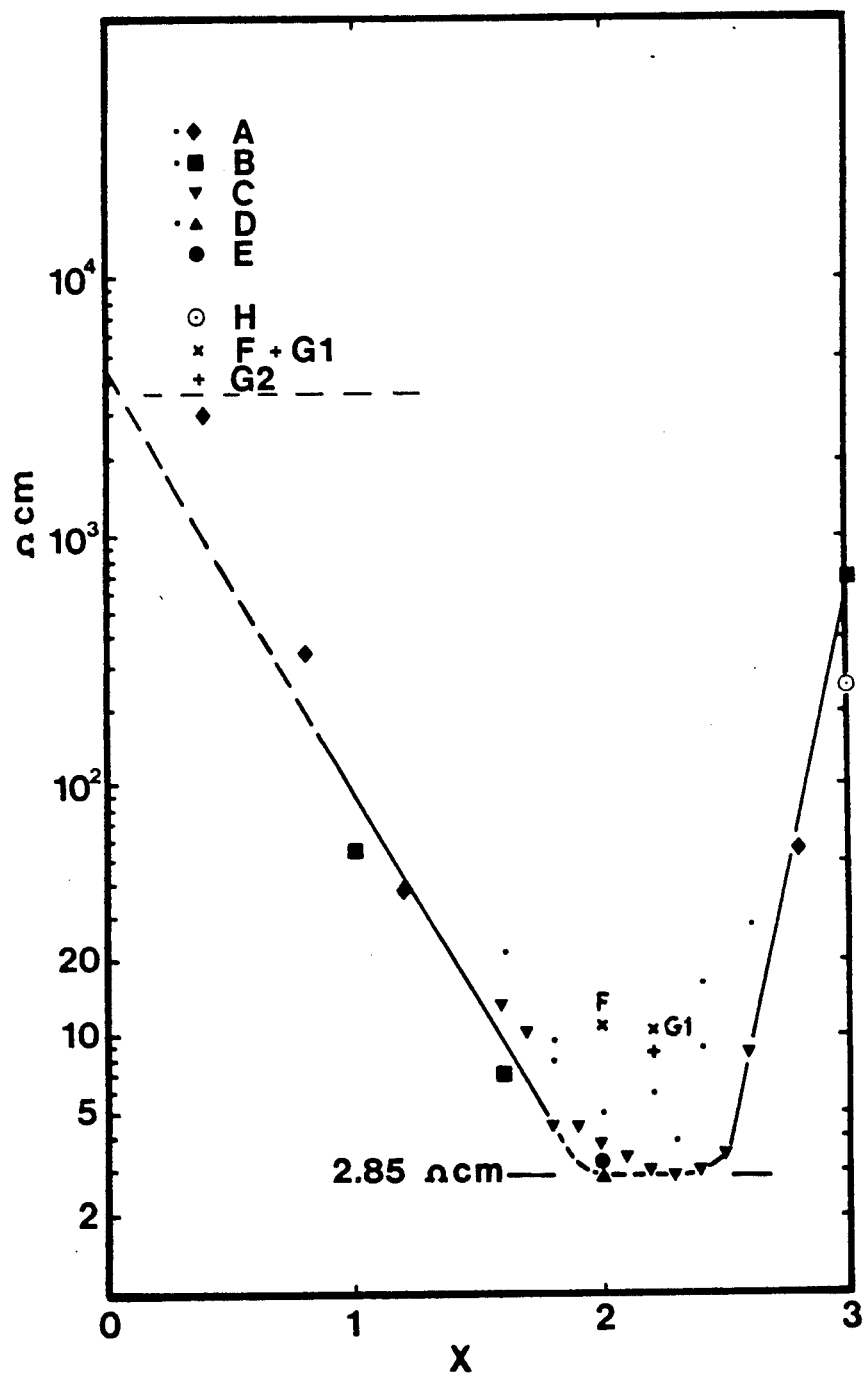
FIG. 12 shows the resistivity of stoichiometric Nasicon and $ZrO_2$-deficient Nasicon (including NZPS-82-1BC) at 300° C.

FIG. 12 shows the resistivity at 300° C. of three materials prepared by the process of the invention and marked E, F and G, respectively. For comparison, data from the literature (A, B, C, D and H) are included. Samples A, B, C, D and E are of the general formula $Na_{1+x}Zr_2P_{3-x}Si_xO_{12}$. The data marked A are according to Mat. Res. Bull. 11, 1976, pp. 203-220, the data B according to Mat. Res. Bull. 14, 1979, pp. 1469-1477, the data C according to "Ion Transport in Solids, Electrode and Electrolytes", Elsevier 1979, pp. 419-422, and the data D according to Solid State Ionics 3/4, 1981, pp. 243-248. Samples F, G and H are of the general formula $Na_{1+y}Zr_{2-z}P_{3-x}Si_xO_{12-a}$. The data marked H are according to Solid State Ionics 7, 1982, pp. 345-348. The abscissa axis shows the factor x from the general formulae.

As mentioned above, the raw material for the polycrystalline material is prepared by controlled mixing and reaction between the alkoxides of Na, Zr, Si and optionally Al and with dry phosphoric acid in an alcohol with addition of water. The alkoxides employed comprise methylates, ethylates, propanolates and butylates. The alcohols employed comprise ethanol and propanol.

The problems associated with the preparation of the alkoxide based gels are as follows:
(1) To limit the reactivity of the phosphoric acid towards the Zr-alkoxide. The problem is greater when using $Zr(OEt)_4$ than when using $Zr(OBut)_4$.
(2) To avoid precipitation of heavily soluble phosphates of Zr and Na in alcohol solutions.
(3) To avoid precipitation of heavily soluble Zr-alkoxide-Na-alkoxide compounds. This is especially a problem in the use of ethanol and ethanolates.

(4) To control the copolymerisation of Si(OR)$_4$ and Zr(OR)$_4$ (where R is the "hydrocarbon moiety" of an alcohol), so that there will not be formed inhomogenities because of the difference in rate of hydrolysis between the two components.

Apart from depending on the selection of the starting chemicals (methylate, ethylate, etc.), the properties of the resulting gels depend on the concentration of alkoxide in the alcohol used as solvent, on the ratio between alkoxide and added water which is to bring about the final hydrolysis and gelling, and on the temperature at which the gelling is performed.

The reactions which take place in the mixed alkoxide solution are, inter alia of the following types ($M^{n+}$ metal ion of the valency n, $OR^-$ =alkoxide group):

$$M^{n+}(OR^-)_n + H_3PO_4 \rightarrow M^{n+}(OR^-)_{n-1}H_2PO_4 + HOR \quad (I)$$

$$M^{n+}(OR^-)_n + H_2O \rightarrow M^{n+}(OR^-)_{n-1}OH + HOR \quad (II)$$

$$M_1{}^{n1+}(OR_1{}^-)_{n1-1}OH + M_2{}^{n2+}(OR_2{}^-)_{n2} \rightarrow (^-R_1O)_{n1-1}M_1{}^{n1+} - O - M_2{}^{n2+}(OR_2{}^-)_{n2-1} + HOR \quad (III)$$

$$2M^{n+}(OR^-)_{n-1}OH \rightarrow (^-RO)_{n-1}M^{n+} - O - M^{n+}(RO^-)_{n-1} + H_2O \quad (IV)$$

The following examples describe preferred embodiments of the method of the invention in greater detail:

EXAMPLE 1

Preparation of a Metal Alkoxide Gel

Anhydrous phosphoric acid in an amount corresponding to 0.1078 mole was dissolved in 30 ml of ethanol containing 0.2961 mole of water. To this solution was added 0.2961 mole of tetraethylorthosilicate containing 30 ml of ethanol at room temperature. The reaction mixture was left to react for 16 hours at room temperature followed by addition of 0.2006 mole of zirconium-tetra-n-propoxide from a 95% stock solution in propanol and 0.3955 mole of sodium ethoxide from a 1.5M stock solution in ethanol. The mixture turned opaque, but no precipitation occurred. The mixture was then left to react for 16 hours at room temperature. Then, the solution was gelled by addition of 2 moles of water dissolved in 36 ml ethanol. The gelling was performed at room temperature, after which the temperature was raised to 80° C. for 24 hours.

The resulting gel (NZPS-82-1BC; cf. Table 1) was dried at 110° C. in a vacuum drying cupboard for 24 hours and was then crushed. The resulting product was by means of X-ray diffraction shown to be amorphous and had a large specific surface area of 94 m$^2$/g as determined by the BET-method. The amount of alkoxide remaining in the gel (converted to CO$_2$ by burning) corresponded to 4% by weight of CO$_2$.

The gels NZPS-81-1, NZPS-81-3, NZPS-81-4, NZPS-81-5, NZPS-82-1A and NZPS-82-2 (cf. Table 1) were also prepared according to this method, consideration being had to their different chemical composition.

EXAMPLE 2

Preparation of a Metal Alkoxide Gel

Anhydrous phosphoric acid in an amount corresponding to 0.1 mole was dissolved in 60 ml of i-propanol. 0.2 Mole of tetraethylorthosilicate was diluted with 40 ml of i-propanol. The two solutions were mixed. After 5 minutes at room temperature, the first proton of the phosphoric acid had reacted completely with the tetraethylorthosilicate. Then, 0.2 mole of zirconium-tetra-n-propoxide diluted with 260 ml isopropanol were added. The mixture was left to react for 16 hours at room temperature followed by addition of 0.2 mole of water dissolved in 180 ml of iso-propanol. The mixture was left to react for 1 hour at room temperature followed by addition of 0.3 mole of sodium methoxide from a 1.54N solution in methanol.

The resulting solution was clear and of low viscosity. When the solution is kept isolated from the atmosphere and from other sources of humidity, it is stable for at least one year and does not gel. On standing for about 100 hours at room temperature exposed to the atmosphere, it gelled to a slightly yellow, but clear gel. When the solution was gelled as a monolith by addition of 1.5 moles of water dissolved in 50 ml of i-propanol at room temperature, a clear gel was obtained (cf. NZPS-82-XA in Table 1). The gel NZPS-83-2C was prepared in the same manner, consideration being had to its different chemical composition.

EXAMPLE 3

Preparation of a Metal Alkoxide Gel 18 millimoles of tetraethylorthosilicate, 16.7 millimoles of zirconium-tetra-n-propoxide, 34 millimoles of sodium methoxide (1.54M in methanol) and 15 ml of n-propanol were mixed and heated at reflux for 3 hours. Upon cooling, a mixture of 4 millimoles of phosphoric acid and 8 millimoles of tetraethylorthosilicate dissolved in 0.75 mole of i-propanol was added. The mixture was heated at reflux for 2.5 hours. Upon cooling, 5 ml of water diluted with 30 ml methanol were added with stirring. The resulting clear solution gelled within ½ hour after the addition to a clear, slightly opalescent gel. The resulting gel had an oxide composition corresponding to Na$_{3.4}$Zr$_{1.67}$Si$_{2.6}$P$_{0.4}$O$_{10.84}$.

EXAMPLE 4

Preparation of a Metal Alkoxide Gel

A mixture of 10 millimoles of tetraethylorthosilicate, 20 millimoles of zirconium-tetra-n-propoxide, 20 millimoles of sodium methoxide (1.54M in methanol) and 10 ml of n-propanol were heated at reflux for 3 hours. Upon cooling, a mixture of 10 millimoles of phosphoric acid and 10 millimoles of tetraethylorthosilicate dissolved in 0.3 moles of isopropanol was added dropwise. The resulting solution was clear. The solution was gelled by addition of water substantially as described in Example 3. The resulting gel had an oxide composition corresponding to Na$_2$Zr$_2$PSi$_2$O$_{11.5}$.

EXAMPLE 5

Preparation of a Metal Alkoxide Gel 0.44 mol of tetraethylorthosilicate was reacted with 0.16 mol of anhydrous phosphoric acid dissolved in 100 ml of n-propanol. The resulting mixture was added to 0.298 mole of zirconium-tetra-n-propoxide diluted with 400 ml of n-propanol. After reaction overnight, 0.298 mole of water diluted to 125 ml with methanol was dded dropwise. The resulting solution was clear. To the clear solution, a solution of 0.588 mole of sodium acetate and 0.68 mole of acetic acid in 360 ml methanol was added. The resulting clear solution was gelled by addition of water in i-propanol. The resulting gel had an oxide composition corresponding to Na$_{2.94}$Zr$_{1.49}$Si$_{2.2}$P$_{0.8}$O$_{10.85}$.

TABLE 1

Compositions after calcination of gels prepared according to the invention

| | % by weight | | | | |
|---|---|---|---|---|---|
| | P$_2$O$_5$ | SiO$_2$ | ZrO$_2$ | Al$_2$O$_3$ | Na$_2$O |
| NZPS-79-6.4, 2.1* | 14.53 | 24.60 | 39.60 | — | 19.64 |
| NZPS-81-3 | 16.19 | 20.55 | 46.82 | — | 16.44 |
| NZPS-81-1 | 13.41 | 22.64 | 46.41 | — | 17.55 |
| NZPS-82-2 | 7.91 | 26.78 | 45.76 | — | 19.56 |
| NZPS-82-1A | 12.24 | 28.47 | 39.59 | — | 19.70 |
| NZPS-82-1BC** | 12.25 | 28.51 | 39.60 | — | 19.64 |
| NZPS-81-5 | 10.46 | 29.11 | 40.23 | — | 20.20 |
| NZPS-82-XA | 13.38 | 22.65 | 46.45 | — | 17.52 |
| NZPS-81-4 | 13.38 | 22.66 | 46.42 | — | 17.54 |
| NZPS-82-3 | 13.36 | 22.66 | 46.41 | — | 17.57 |
| NZPS-83-2C | 5.83 | 31.33 | 41.52 | — | 21.32 |
| NZPSA-83-1 | 10.76 | 28.66 | 39.78 | 1.12 | 19.69 |

*The material shown in FIG. 1. Made from mixture of oxides according to the method described in Material Research Bulletin 11, 1976, p. 173. Not according to the invention.
**The material shown in FIG. 2.

EXAMPLE 6

Preparation of a Metal Alkoxide Gel 0.26 mol of tetraethylorthosilicate was reacted with 0.04 mol of anhydrous phosphoric acid dissolved in 100 ml of n-propanol. The resulting mixture was added to 0.2 mol of zirconium-tetra-n-propoxide dissolved in 250 ml of n-propanol. After reaction overnight, 0.2 mol of water diluted to 60 ml with methanol was added. The resulting solution was clear. To this clear solution, a solution of 0.36 mol of sodium nitrite dissolved in 850 ml of methanol was added. This resulted in the formation of a white, fine-grained precipitate which dissolved after addition of 640 ml of methanol and standing for about 36 hours with stirring. The resulting clear solution was gelled by addition of water in methanol substantially as described in Example 2. The oxide composition of the resulting gel corresponds to:

Na$_{3.6}$Zr$_{2.0}$Si$_{2.6}$P$_{0.4}$O$_{12}$.

EXAMPLE 7

Preparation of a Metal Alkoxide Gel

To a clear solution made from the same amounts of tetraethylorthosilicate, zirconium-tetra-n-propoxide and anhydrous phosphoric acid as described in Example 6, 0.36 mol of sodium nitrate, 47 ml of water and 5.6 ml of concentrated nitric acid in 1800 ml of methanol was added. A milky solution containing a white precipitate was obtained. Upon addition of water, a slow gelling was observed. The gel has an oxide composition corresponding to Na$_{3.6}$Zr$_{2.0}$Si$_{2.6}$P$_{0.4}$O$_{12}$.

EXAMPLE 8

Preparation of Aluminum-containing Nasicon Gel 0.238 mol of tetraethylorthosilicate was reacted with 0.0758 mol of anhydrous phosphoric acid dissolved in 100 ml of n-propanol by mixing. 0.161 mol of zirconium-tetra-n-propoxide was reacted with 0.0110 mol of aluminum-sec.butoxide. A white precipitate was immediately formed. After addition of 200 ml of n-propanol and stirring, this precipitate dissolved again, and after 2.5–3 hours, the solution was clear again.

Thereafter, the tetraethylorthosilicate-phosphoric acid mixture was added to the zirconium-tetra-n-propoxide-aluminum-sec.butoxide mixture, and the resulting solution, which was clear, was allowed to stand overnight with stirring.

A 1:10 mixture of H$_2$O and n-propanol was added dropwise. Thereby, a white precipitate was formed. Immediately upon formation of the precipitate, 0.317 mol of sodium methoxide dissolved in 200 ml of methanol was added. After about 3 hours of stirring, the solution was clear. Thereafter, the solution was gelled homogeneously by addition of water dissolved in n-propanol in the usual manner. Prior to the gelling, the total oxide concentration in the solution was 7.9% by weight. The solution was gelled by addition of 35 ml of water diluted in 300 ml of methanol. The resulting gel (NZPSA-83-1) was clear and had an oxide composition corresponding to:

Na$_{2.93}$Zr$_{1.61}$(Al$_{0.1}$Si$_{2.20}$P$_{0.70}$)O$_{10.74}$.

EXAMPLE 9

Shaping Articles of Ceramic Material

For the preparation of green bodies for later conversion into ceramics, the dried gel powders prepared by the process described in Examples 1–8 may either be used directly as a powder for pressing and shaping by conventional pressing methods, or they may first be calcinated at temperatures up to 710° C. The calcination results in the removal of the remainder of water and organic material from the gel. The variation in the properties of gel powders prepared as described above is illustrated in Table 2. For NZPS-82-1BC, the specific gravity of the dried powder and the calcinated powder is shown in FIG. 9 together with the bulk density of tablets (diameter of about 1 cm) produced from the gel, as a function of the pressure at which the tablets are shaped and of the preceding treatment of the powder.

The clear gel monoliths prepared by the process described in Examples 2–4 and 8 may either be dried and powdered and used as described above, or they may be dried carefully, e.g. at room temperature over a period of 7 days. In this case, the gels retain their monolithic shape and shrink without disintegrating into a powder. Thus, it is possible to cast mouldings directly by means of the solutions prepared in these examples by pouring them into a mould of the desired shape of the final article, but enlarged to compensate for the shrinkage, before gelling.

EXAMPLE 10

Sintering Shaped Articles of Ceramic Material

The course of sintering of the dried gel NZPS-82-1BC as a function of temperature is shown in FIG. 8. The bulk density and porosity of the resulting articles when sintered to 1100±20° C. is shown in FIG. 10 as a function of the pressure used to compress the articles. It was demonstrated that the strongest sintering of this gel occurs in a narrow range between 800° C. and 900° C., and that the highest bulk density of the sintered plates surprisingly occurs at a low compression pressure. The other types of gel prepared according to the method described in Examples 1–8 show similar characteristics. Thus, all the compositions studied show enhanced sintering in this temperature interval, but the absolute magnitude of the densification decreases as the ZrO$_2$ content increases. The competing processes which control the sintering behaviour in this interval appear to be viscous flow in the glass phase and crystal growth. For stoichiometric Nasicon compositions, densities in excess of 93% of the theoretical were only obtained by sintering to temperatures close to the incongruent melting point (FIG. 4).

In order to avoid cracking due to too rapid sintering, it is necessary to heat slowly. The gel NZPS-82-1BC dried at 110° C. is suitably heated from 20° C. to 710° C. over a period of 6 hours, from 710° C. to 1000° C. over a period of 14 hours, from 1000° C. to 1100° C. over a period of 2 hours, and at 1100° C. for 9 hours.

The two final steps are not necessary for the sintering, but they are necessary in order to obtain the maximum crystallinity of the material.

The crystalline equilibrium phases at 1150° C. as determined by X-ray diffraction in the various compositions stated in the examples are shown in Table 3. The flexural and tensile strength of ceramic material prepared by the process described above and determined by the three-point method is shown in FIG. 11.

The resistivity with respect to sodium ion conductivity obtained with polycrystalline ceramic articles of the composition stated above are shown in Table 4.

The temperature interval for maximum sintering of some gels appears from Table 5.

TABLE 2

Variation in properties of gels prepared by reaction polymerization

| Gel No. | organics determined as $CO_2$ % by weight | specific density g/cm³ | specific surface area determined by BET m²/g | Comments | | |
|---|---|---|---|---|---|---|
| Vacuum dried 110° C. NZPS- | | | | | | |
| 82-3 | — | — | 2.6 | spray dried | | |
| 82-2 | 5.1 | — | 109 | original | | |
| | 1.7 | 2.78 | 77 | rehyd. 25–80° C. | | |
| 82-4 | — | — | 127 | | | |
| 82-1A | 4.9 | 2.59 | 50 | | | |
| 82-1BC | 6.3 | — | 136 | original | | |
| | 3.6 | 2.62 | 103 | rehyd. 25° C. | | |
| 83-2C | — | — | 231 | dest. in steps* | | |
| Calcined | | | | °C. | h | |
| 82-3 | — | 3.25 | 2.1 | 710 | 100 | grey |
| 82-2 | 0.7 | 3.26 | 15 | 710 | 160 | grey |
| 82-4 | — | 2.87 | 5.6 | 710 | 140 | white |
| 82-1BC | — | — | 50 | 500 | 142 | grey |
| | — | — | 40 | 550 | 161 | grey |

TABLE 2-continued

Variation in properties of gels prepared by reaction polymerization

| Gel No. | organics determined as $CO_2$ % by weight | specific density g/cm³ | specific surface area determined by BET m²/g | Comments | | |
|---|---|---|---|---|---|---|
| | <0.1 | 3.11 | 14 | 710 | 160 | white |

*$H_2O$ added to the partially dried gel.

TABLE 3

Equilibrium Phases at 1150° C. Determined by X-ray Diffraction

| | Nasicon $Na_{1+x}Zr_2P_{3-x}Si_xO_{12}$ x | Other Phases |
|---|---|---|
| NZPS-81-3 | 1.8 | — |
| NZPS-81-1 | 2.0 | — |
| NZPS-82-2 | 2.4 | — |
| NZPS-82-1BC | 2.14 | Vlasovite ($Na_2ZrSi_4O_4$) |
| NZPS-81-5 | 2.25 | Vlasovite ($Na_2ZrSi_4O_4$) Parakeldyshite ($Na_2ZrSi_2O_4$) |
| NZPS-82-XA | 2.0 | — |

TABLE 4

Specific resistivity in Nasicon ceramics measured by the AC-method (blocking Au-electrodes) or by DC in Na/Na-cells

| Comp. no. | °C. | h | bulk density g/cm³ | 25° C. AC | 125° C. AC | 125° C. DC | 175° C. AC | 175° C. DC | 250° C. AC | 250° C. DC | 300° C. AC | 300° C. DC | 350° C. DC | 400° C. DC |
|---|---|---|---|---|---|---|---|---|---|---|---|---|---|---|
| NZPS- | | | | | | | | | | | | | | |
| 82-2 | 1180 | 0.2 | 3.24 | 340 | 25 | — | 11 | — | 8 | — | 6 | — | — | — |
| 81-1 | 1010¹ | 0.1 | 3.26 | 3290 | 177 | — | 68 | — | 33 | — | 24 | — | — | — |
| | 1250¹ | 0.1 | 3.19 | 1128 | 41 | — | 10 | — | 5 | — | 3.3 | — | — | — |
| 81-3 | 1250¹ | 0.1 | — | 1596 | 57 | — | 26 | — | 16 | — | — | — | — | — |
| 81-5 | 1260¹ | 0.1 | — | 628 | 50 | — | 22 | — | — | — | — | — | — | — |
| 79-6,4,2.1 | 1226 | 6³ | — | 5680 | 132 | — | 41 | — | 16 | — | 11 | — | — | — |
| 82-1BC | 1100² | 3 | 3.10 | — | — | 162 | — | 49 | — | 17 | — | — | — | — |
| | 1100 | 9 | 3.06 | 3653 | 162 | — | 52 | — | 20 | 18 | 13 | 11.3 | 7.7 | 4.9 |
| | 1200 | 3⁴ | 3.01 | 2268 | 129 | — | 51 | — | 18 | 12 | 10.6 | 8.6 | 6.7 | 5.5 |
| 82-1-A01 | 1205 | 10 | 2.908 | 1254 | 62 | — | 22 | — | 9.8 | — | 7.0 | — | — | — |

¹Hot-pressed 60 MPa,
²Hot-pressed 30 MPa,
³after 16 h at 1201° C.
⁴after 9 h at 1100° C.

TABLE 5

Temperature Interval for Maximum Sintering of the Prepared Gels Dried at 110° C. and Sintered in Atmospheric Air

| | Bulk density g/cm³ Green Sintered | | Interval Maximum Sintering $T_1-T_2$° C. | Relative Sintering in % at Temperature | | |
|---|---|---|---|---|---|---|
| | | | | <$T_1$ | $T_1-T_2$ | $T_2$< |
| NZPS-81-1 | 1.55 | 2.94 | 860–970 | 38 | 59 | 3 |
| NZPS-82-1BC | 1.074 | 3.06 | 800–885 | 23 | 70 | 7 |
| NZPS-81-5 | 1.58 | 2.88 | 845–990 | 42 | 68 | 0 |

EXAMPLE 11

Electrochemical tests

The ion conductivity of the ceramic material based on NZPS-82-1BC sintered to 1100° C. for 9 hours was determined by the AC-method. In sodium/sodium cells, the ceramic material was subjected to current densities of up to 0.8 A/cm² for brief periods. No decomposition of the ceramic material was observed. After a period of up to 1136 hours in sodium/sodium cells at 300° C., the ceramic material showed no signs of decomposition apart from a brownish staining of the surface.

Static corrosion experiments to determine the durability of the ceramic material in molten sodium were conducted on the ceramic material based on NZPS-82-1BC sintered to 1100° C. for 9 hours.

The results are shown in Table 6.

TABLE 6

Data on the corrosion of Nasicon in liquid sodium $M_t$ = Observed weight loss, mg/cm².
$M_o$ = Weight loss due to temperature independent fast reaction.
$K_{Na}$ = $(M_t - M_o)/(h \times d)$; d = 3.00 g/cm³.

NZPS-82-1BC sintered to 1120° ± 20° C.

| temp. °C. | time h | $M_t$ mg/cm² | $M_o$ mg/cm² | $M_t-M_o$ mg/cm² | $K_{Na}$ $10^4$/cmh |
|---|---|---|---|---|---|
| 400 | 6 | 1.42 | — | — | — |
| 400 | 48 | 1.45 | — | — | — |
| 400 | 96 | (2.07) | — | — | — |
| 400 | 144 | 1.45 | — | — | — |
| 400* | 36 | 0.33 | — | 0.33 | 0.031 |
| 450 | 96 | 4.24 | 1.44 | 2.90 | 0.097 |
| 500 | 6 | 0.95 | — | (0.95) | (0.53) |
| 500* | 12 | (3.28) | — | (3.28) | (0.91) |
| 500 | 72 | 14.04 | 1.44 | 12.60 | 0.58 |
| 550 | 7 | 9.09 | 1.44 | 7.65 | 3.6 |
| 600 | 6 | 21.33 | 1.44 | 19.89 | 11.1 |
| 650* | 4 | 7.94 | — | 7.94 | 6.62 |
| 650 | 4 | 30.23 | 1.44 | 28.79 | 24.0 |
| 700 | 6 | 67.77 | 1.44 | 66.33 | 36.9 |

*surface exposed to the atmosphere removed immediately before experiment.

Corrosion tests were also performed on ceramics of the same composition, but sintered to 1200° C. for 10 hours. This ceramic showed a higher resistance to sodium corrosion; thus, no corrosion was observed at 400° C.

EXAMPLE 11

The Use of NZPS-82-1BC for Sodium-Sensitive Measuring Electrodes

Potentiometric membrane electrodes as shown in FIG. 1 were prepared from the above mentioned material by melting a polycrystalline slide thereof ($\phi$5 mm×2 mm) in a glass tube (1) with a coefficient of expansion corresponding to the ceramic membrane (2). An electrolyte solution (3) consisting of 0.2M NaCl stabilized at pH 7 with citrate buffer is filled into the glass moiety, and a silver/silver chloride electrode as a so-called inner reference (4) is immersed in the solution. As reference electrode (5) for the membrane electrodes, a conventional calomel electrode (S.C.E.) is used, which by means of a salt bridge of saturated potassium chloride is in contact with the sample solution (6), which is to be measured by the membrane electrodes. The measurements are performed using a pH-meter (7), which functions as a high impedance mV-meter, but in view of the low resistivities of the electrodes (1–10 kohm) it would also be possible to perform the measurements with relatively low impedance measuring instruments.

The mV-signals at 25° C. were recorded for 4 test electrodes in the following solutions: 0.1M NaCl, 1 mM NaCl, 1 mM HCl and 0.1M KCl.

| | Measuring results: | | | |
|---|---|---|---|---|
| | El. 1 | El. 2 | El. 3 | El. 4 |
| 0.1 M NaCl | −8 mV | −11 mV | −4 mV | −4 mV |
| 1 mM NaCl | −80 mV | −80 mV | −120 mV | −97 mV |
| 1 mM HCl | −36 mV | −38 mV | −48 mV | −49 mV |
| 0.1 M KCl | −62 mV | −61 mV | −96 mV | −91 mV |
| $K_{NaH}$ | 15 | 14 | 15 | 10 |
| $K_{NaK}$ | 0.04 | 0.04 | 0.03 | 0.07 |

The selectivity factors are calculated from the Nicholsky-equation:

$$E = E_1 + S \cdot \log (a_{Na} + K_{Nax} \cdot a_x)$$

Compared to conventional solid-state sodium-sensitive electrodes, the electrodes with NZPS-82-1BC especially show a surprisingly good selectivity versus hydrogen ions. Another advantage is the low membrane resistance of the electrodes, which makes it possible to prepare both robust and miniaturized sodium-sensitive electrodes.

We claim:

1. A method for selectively determining the concentration or activity of a particular cation species in a medium also containing other cation species, said method comprising (a) contacting the medium with an ion-sensitive measuring electrode device comprising (i) an ion-sensitive solid element with selectivity to the particular cation and (ii) a reference system, and (b) determining the concentration or activity of the particular cation, the ion-sensitive element comprising ion-conductive crystalline material based on (a) oxides of an alkali metal, zirconium, phosphorus, and optionally aluminum; or
   (b) oxides of an alkali metal, zirconium, silicon, and optionally aluminum; or
   (c) oxides of an alkali metal, zirconium, phosphorus, silicon, and optionally aluminum;

the crystal structure of which comprises a three-dimensional interstitial space comprising positions for the particular cation.

2. The method according to claim 1, characterized in that the ion is an alkali metal ion and that the crystalline material comprises $M_{1+x}Zr_2Si_xP_{3-x}O_{12}$, where $0 \leq x \leq 3$, and M designates an alkali metal, or $ZrO_2$-deficient $M_{1+x}Zr_2Si_xP_{3-x}O_{12}$.

3. The method according to claim 1 and adapted for the determination of Na+ ions, characterized in that the ion-sensitive element of ion-conducting crystalline material comprises Nasicon, $Na_{1+x}Zr_2Si_xP_{3-x}O_{12}$, $0 \leq x \leq 3$, or $ZrO_2$-deficient Nasicon.

4. The method according to claim 1, characterized in that the ion-sensitive element comprises $ZrO_2$-deficient Nasicon with the forumula:

$Na_{2.94}Zr_{1.49}Si_{2.2}P_{0.8}O_{10.85}$.

5. The method according to claim 1, characterized in that the ion-sensitive element comprises a crystalline material of the general formula $Na_{1+x+y+2a}Zr_{2-z}P_{3-x}Si_xAl_aO_{12-2z+y/2}$, wherein
$0 \leq x \leq 3$,
$0 \leq z \leq x/3$,
$0 \leq a \leq (3-x)/2$
$-0.3 \leq y \leq 0.3$.

6. The method according to claim 5 in which $0 \leq a \leq 0.4$.

7. The method according to claim 1, characterized in that the polycrystalline, ion-conducting material has a dense structure with a bulk density of >95% of the specific gravity of the phases involved.

8. An ion-sensitive measuring electrode device comprising (a) an ion-sensitive solid element with selectivity to a particular cation and (b) a reference system, the ion-sensitive element comprising an ion-conductive crystalline material based on
   (a) oxides of an alkali metal, zirconium, phosphorous, and optionally aluminum; or
   (b) oxides of an alkali metal, zirconium, silicon, and optionally aluminum; or
   (c) oxides of an alkali metal, zirconium, phosphorous, silicon, and optionally aluminum;
the crystalline material having a crystal structure comprising a three-dimensional interstitial space having positions for the particular cation, the ion-sensitive element further comprising a surface adapted to be brought in contact with a sample in which the activity or concentration of the particular cation species is to be determined, the reference system comprising an internal reference electrode and a liquid or gelled electrolyte, the liquid or gel electrolyte being in contact with both the internal reference electrode and with the ion-sensitive element.

9. An ion-sensitive electrode device according to claim 8 in which the crystalline material of the ion-sensitive element comprises $M_{1+x}Zr_2Si_xP_{3-x}O_{12}$, where $0 \leq x \leq 3$, and M designates an alkali metal, or $ZrO_2$-deficient $M_{1+x}Zr_2Si_xP_{3-x}O_{12}$, and which is prepared by preparing a gel by controlled mixing, in an organic medium, of anhydrous phosphoric acid with lower alkoxides of zirconium, silicon, sodium, and optionally a lower alkoxide of aluminum, the alkali metal component alternatively being an alkali metal salt soluble in the organic medium, followed by gelling by addition of water, removing water and volatile components from the gel, and converting the water- and volatiles-free gel to a crystalline material.

10. An ion-sensitive electrode device according to claim 9 in which the gel is prepared by reacting anhydrous phosphoric acid dissolved in a lower alcohol with a lower alkoxide of silicon, reacting the resulting polymer with lower alkoxides of zirconium and of the alkali metal dissolved in a lower alcohol and optionally with a lower alkoxide of aluminum, and gelling the resulting mixture by addition of water; or by reacting anhydrous phosphoric acid dissolved in a lower alcohol with a lower alkoxide of silicon, adding the resulting polymer to a refluxed mixture comprising a lower alkoxide of silicon, zirconium, the alklai metal, and optionally a lower alkoxide of aluminum, and gelling the resulting mixture by addition of water.

11. An electrode device according to claim 10, characterized in that the ratios between the starting materials used result in a polycrystalline material of Nasicon- or $ZrO_2$-deficient Nasicon-type with $1.8 \leq x \leq 2.4$.

* * * * *

UNITED STATES PATENT AND TRADEMARK OFFICE
CERTIFICATE OF CORRECTION

PATENT NO. : 4,686,012

DATED : Aug. 11, 1987

INVENTOR(S) : John E. Engell et al.

It is certified that error appears in the above-identified patent and that said Letters Patent is hereby corrected as shown below:

Column 1, line 9: "PCT/OK" should read --PCT/DK--

Column 4, line 29: "are" should read --is--

Column 8, line 64: "dded" should read --added--

Column 14, line 54: "forumula" should read --formula--

Column 16, line 3: "sodium" should read --an alkali metal--

Signed and Sealed this

Twenty-ninth Day of November, 1988

Attest:

DONALD J. QUIGG

Attesting Officer

Commissioner of Patents and Trademarks